United States Patent [19]

Wassiliew, deceased et al.

[11] Plant 4,748

[45] Jun. 30, 1981

[54] DWARF PEACH W-110

[75] Inventors: Fedor Wassiliew, deceased, late of Orange, Calif.; by Nicolaus Wassiliew, heir, Costa Mesa, Calif.; by Alexander Wassiliew, heir; by Marsha W. Hartman, heir, both of Orange, Calif.; by Valentina Wassiliew, heir, Costa Mesa, Calif.

[73] Assignee: Jackson & Perkins Co., Medford, Oreg.

[21] Appl. No.: 145,675

[22] Filed: May 1, 1980

[51] Int. Cl.[3] ..... A01H 5/03

[52] U.S. Cl. ..... Plt./42

[58] Field of Search ..... Plt./42

*Primary Examiner*—Robert E. Bagwill

*Attorney, Agent, or Firm*—Klarquist, Sparkman, Campbell, Leigh, Whinston & Dellett

[57] ABSTRACT

A vigorous genetically dwarf peach tree which is distinguished particularly by its degree of dwarfness, single or partly double light pink flowers, late July ripening date and rounded fruit with pale yellow, red flushed skin. The flesh is sweet and white with red streaks.

3 Drawing Figures

1

This present invention relates to a new and distinct variety of peach tree of the genetically dwarf type, having light pink flowers and freestone, white fleshed fruit. The original seedling of this new peach was discovered by Fedor Wassiliew, among seedlings grown from various crosses made by Mr. Wassiliew in Orange, Calif. The exact parentage is unknown.

The primary objective of the breeding program was to produce a variety of dwarf peach, usable as an ornamental plant in home gardens and producing an edible, tasteful fruit of good texture and juice content. This objective was fully achieved, along with other desirable features, as evidenced by the following unique combination of characteristics which are outstanding in this new variety and which distinguish it from all other varieties:

1. A vigorous plant of dwarf character, attaining less than three feet height in four growing seasons.
2. An abundance of single or partially doubled light pink flowers.
3. Ripening date at Irvine, Calif. approximately July 20th.
4. Round, red flushed, pale yellow fruit with a shallow suture.
5. Moderate fruit set at Irvine, Calif.
6. Firm, white flesh, red around the stone cavity and streaked throughout with red.

Asexual reproduction of this new peach variety as performed by budding at Wasco, Calif., shows that the foregoing characteristics are established and come true to form through succeeding propagations.

The accompanying illustrations show typical specimens of the plant, leaves, flowers, fruit and seed of this new variety depicted in color as nearly true as it is reasonably possible to make the same in a color illustration of this character.

The following is a detailed description of this new variety, as based upon observations of specimens grown at Irvine, Calif., with color terminology in accordance with the Royal Horticultural Colour Chart, except where general color terms of ordinary dictionary significance are obvious.

2

PLANT

Habit: Genetically dwarf; internodes less than ¼ inch long; reaching less than 3 feet in height in four years; spreading; often broader than tall.

Chilling requirement: About equal to that of the variety Bonanza, U.S. Plant Pat. No. 2,213, bearing fruit at Irvine, Calif.

Leaves:

*Size.*—Length: approximately 6 to 7 inches; pendulous.

*Color.*—Upper surface: near RHS 131A. Under surface: RHS 131D.

FLOWERS

Blooming habit: Flowers are borne heavily the same time as Bonanza to four or five days later.

Size: Approximately 1¼ inches diameter.

Petalage: 5 to 7 petals.

Color (open flower): Mostly near RHS 62C, slightly darker near petal base.

FRUIT

Ripening date: Near July 20th at Irvine, Calif.

Size: After having been thinned, 2½ to 3 inches in diameter; nearly spherical.

Suture: Very shallow.

Skin:

*Color.*—Near RHS 11D at stem end flushed and speckled with orange; distal end completely flushed with color near RHS 172B.

*Pubescence.*—From moderate to light.

Flesh:

*Flavor.*—Sweet to taste.

*Color.*—Near white except the stone cavity which is near RHS 42A and streaks through the flesh of RHS 42A.

Stone:

*Tenacity of flesh.*—Stone not attached to flesh.

*Color.*—Near RHS 187B.

I claim:

1. A new and distinct variety of peach tree of the genetically dwarf type, substantially as herein shown and described, characterized particulary as to novelty by its unique combination of a vigorous dwarf plant, single or partially double, light pink flowers, late July ripening date, nearly spherical red flushed, pale yellow skin, and sweet, white, red-streaked flesh.

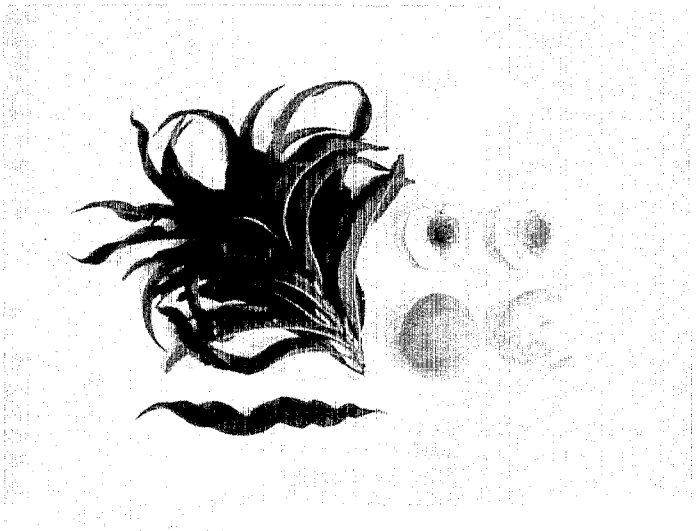
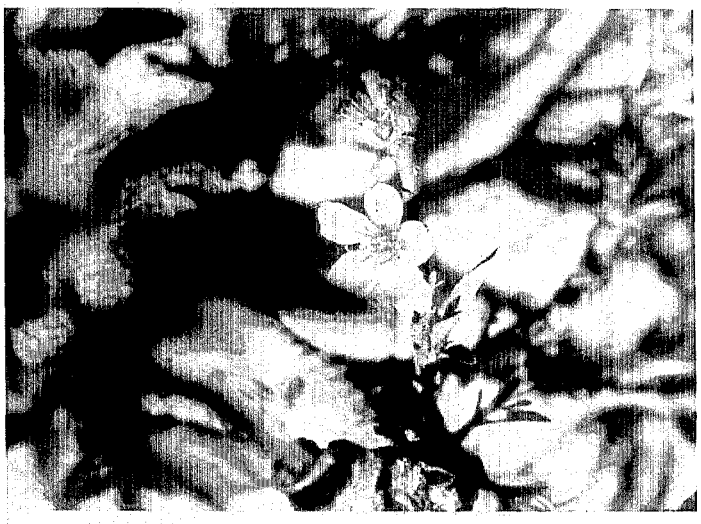
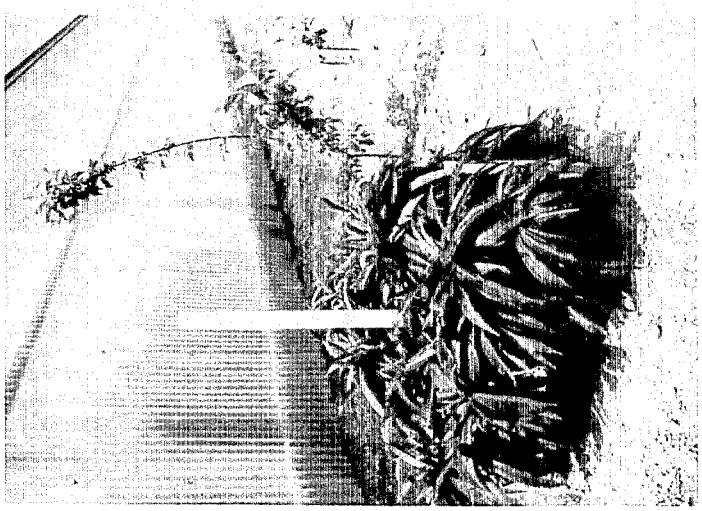

* * * * *